(12) United States Patent
Pottgen et al.

(10) Patent No.: US 6,533,731 B2
(45) Date of Patent: Mar. 18, 2003

(54) METHOD AND APPARATUS FOR MEASURING HEAT FLOW

(75) Inventors: Paul A. Pottgen, Allison Park, PA (US); Neil J. Szuminsky, Pittsburgh, PA (US)

(73) Assignee: Lifecheck, LLC, Pittsburgh, PA (US)

(*) Notice: Subject to any disclaimer, the term of this patent is extended or adjusted under 35 U.S.C. 154(b) by 0 days.

(21) Appl. No.: 09/854,603

(22) Filed: May 15, 2001

(65) Prior Publication Data

US 2002/0173730 A1 Nov. 21, 2002

(51) Int. Cl.⁷ ................................................ A61B 5/00
(52) U.S. Cl. .................... 600/549; 600/587; 600/573; 600/555; 600/306; 374/29; 374/31
(58) Field of Search ............................... 600/306, 309, 600/346, 354, 362, 474, 555, 549, 573, 587; 374/29, 31

(56) References Cited

U.S. PATENT DOCUMENTS

| | | | | |
|---|---|---|---|---|
| 4,345,844 A | * | 8/1982 | Birukoff ........................ 374/31 |
| 4,762,423 A | * | 8/1988 | Basta ........................... 374/31 |
| 5,040,541 A | * | 8/1991 | Poppendiek .................. 128/718 |
| 5,205,170 A | | 4/1993 | Blechinger, et al. | |
| 5,329,812 A | * | 7/1994 | Tada et al. ................. 73/204.21 |
| 5,465,618 A | * | 11/1995 | Yasui et al. ............... 73/204.21 |
| 5,524,618 A | * | 6/1996 | Pottgen et al. .............. 128/633 |
| 5,813,994 A | * | 9/1998 | Pottgen et al. .............. 600/549 |

* cited by examiner

Primary Examiner—Teresa Walberg
Assistant Examiner—Shawntina T. Fuqua
(74) Attorney, Agent, or Firm—Oblon, Spivak, McClelland, Maier & Neustadt, P.C.

(57) ABSTRACT

A method and apparatus for determining caloric expenditure of a subject. The apparatus includes a heat flow sensor having an overlay and/or conductive layer for measuring the evaporative heat loss, in addition to substantially total heat loss, for the subject. The sensor also includes a structure to enhance the migration of perspiration from edges or a bottom of the sensor onto an active region of the sensor. One sensor includes electrodes to effectuate electroendosmosis such that positively biased electrodes are formed at an edge or bottom of the sensor and a negatively biased electrode is formed at a center or top of the sensor. Through electroendosmosis the perspiration is migrated from the positively biased electrodes at the edge or bottom of the sensor to the negatively biased electrode in the center or top of the sensor. Another sensor places thermocouples at edges of a sensing portion to reduce a distance that the perspiration has to migrate. Enhancing the migration of perspiration enhances the measurement of evaporative heat loss. The output of the sensor can also be provided to a device such as a personal computer, a personal digital assistant (PDA), etc.

32 Claims, 6 Drawing Sheets

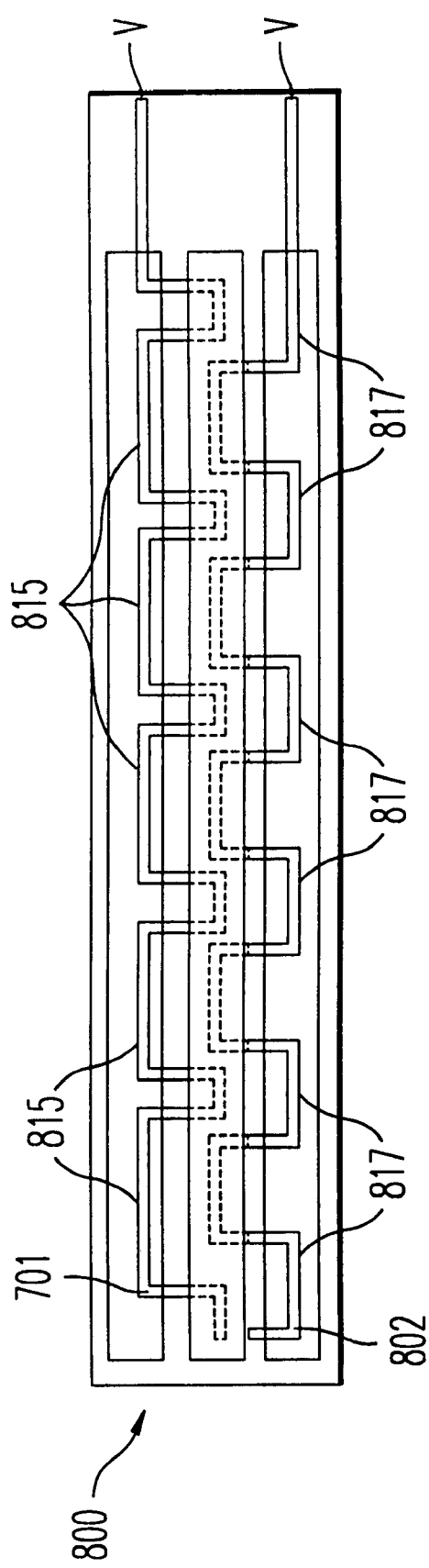
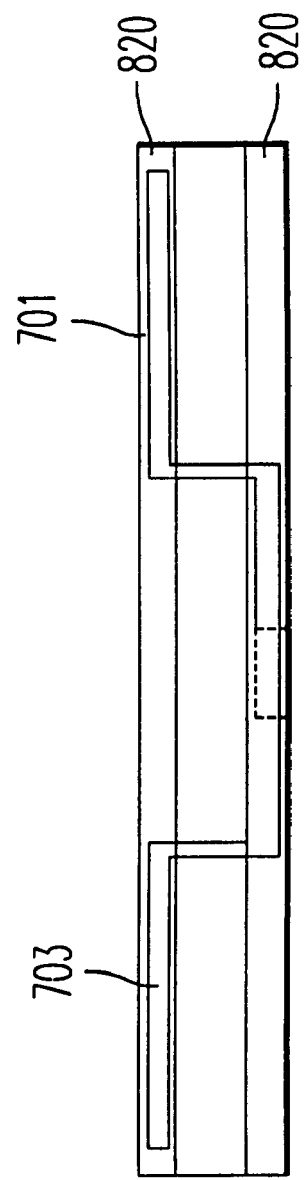
FIG. 8A
FIG. 8B 900
915 915 910 915 915 910

500, 600 — HEAT FLOW SENSOR
1000 — PDA
1010 — DISPLAY

METHOD AND APPARATUS FOR MEASURING HEAT FLOW

BACKGROUND OF THE INVENTION

1. Field of the Invention

The present invention relates to a method and apparatus to measure convective, conductive, radiant, and evaporative heat flow. More specifically, in a preferred embodiment, the invention is used to estimate total heat loss from a human body or other living subject by measuring heat flow from only one or several portions of the body, each of which is assumed to be representative of heat loss over that particular region of the body. From this measurement of total heat flow, a calculation of caloric expenditure can be made.

2. Background of the Invention

The determination of caloric expenditure is an important component of any weight control or fitness program. The number of calories burned is generally estimated through the use of tabulated values for a given activity or by the use of workload measurements on exercise equipment such as treadmills or bikes. Neither, however, is particularly reliable. The tables are generally only average rates for a 70 kg individual performing each activity in some arbitrary, average manner. Certainly not very reflective of any given individual's caloric expenditures, the tables may vary as much as 50% from actual caloric expenditures. Exercise equipment having calorie calculators makes similar errors, and such equipment fails to provide any indication of total caloric expenditure for the day.

A more reliable approach would be to actually monitor the caloric expenditure. The body's metabolic "engines" generate significant amounts of heat; at rest this heat generation is equivalent to that of a 100 watt light bulb. In the human body's attempt to maintain a body temperature of 98.0° F., it controls heat loss to the environment by regulating blood flow to the body surface. At rest, blood flow to the skin is restricted and the surface of the skin may be as much as 20° F. cooler than the body core. This results in a lower flux of heat to the environment. With exercise, however, the excess heat generated by physical exertion (approximately 80% of the energy needed to contract human muscles is wasted as heat) must be dumped to the environment to maintain constant body temperature. Blood flow is diverted to the skin, raising its temperature and the rate at which heat is dumped to the environment is increased.

As a homoiotherm, the body maintains a nearly constant internal body temperature by balancing the generation of heat by its metabolic process with controlled loss of heat through an orchestration of evaporative, convective, radiant, and conductive heat loss mechanisms. At rest in normal room temperature conditions, the body can utilize convective and radiant heat loss (with minor conductive heat loss contributions as well) to regulate body temperature, primarily by control of blood flow to the skin surfaces. If an individual is exercising or is in ambient temperatures above 35° C., the convective and radiant heat loss is inadequate to control internal temperature and the body begins to utilize evaporative heat loss. Evaporation, both that which occurs insensibly (i.e. without obvious sweating) and sensibly (i.e. with obvious sweating) can provide several fold greater heat loss than the other two mechanisms combined.

Heat flow can be accurately measured with a whole body calorimeter. This device is a chamber in which the subject is placed and the total heat given off by the subject's body can be captured and measured. The disadvantages of a whole body calorimeter are that it is expensive, relatively immobile, and the actions and motions of the subject are limited to the space within the chamber. See W. H. Close, M. J. Dauncey, and D. L. Ingram (1980), "Heat loss from humans measured with a direct calorimeter and heat-flow meters", Br. J. Nutr. 43, 87, pp 87–93.

In order to overcome the disadvantages of the whole body calorimeter, a sampling technique using heat flow sensors has been developed to estimate the total heat loss from a subject by measuring heat loss on only a few selected locations on the subject's skin surface. Each measured value is multiplied by a "weighting co-efficient" in order to estimate the heat loss for that particular region of the subject's body. The sum of all regional heat loss components is the estimate of the total heat loss. One system of "weighting coefficients" has been developed by Hardy and DuBois. See Archives of Internal Medicine, Vol. 17, No. 6, pp. 863–871 (1916).

Traditional heat flow sensors are generally based on the measurement of the temperature differential that occurs across a material due to the thermal resistance of that material. In order for the sensor to accurately measure the heat flow, it must not add a significant insulating layer and it must lose heat from its surface in the same manner as the surface on which it is placed. Certain available heat flow sensors perform well on inanimate objects such as walls, doors, boilers, and pipes, where convective, radiant, and conductive heat loss mechanisms predominate. Such heat flow sensors are, however, inadequate for measuring heat loss from the human body, where evaporative heat loss may be significant.

Some current heat flow sensors, such as that produced by RdF, are unable to reliably include the component of evaporative heat loss from the body as part of its output signal. This results in an under estimation of heat loss for two main reasons: 1) such sensors actually occlude the surface of the skin, preventing evaporation, and therefore, any moisture that does move from under the sensor evaporates from the skin surface adjacent to the sensor and not from the sensor surface itself; and 2) when used to monitor body heat loss, as the evaporative heat loss increases from the skin surface, thereby reducing the skin surface temperature, these sensors actually show a decreased heat flow.

OBJECTS OF THE INVENTION

A first object of the present invention is to provide a novel heat flow sensor capable of accurately measuring all components of heat loss, including evaporative heat loss.

A further and more specific object of the present invention is to provide a novel sensor design in the novel heat flow sensor which is particularly well suited to ensure that evaporative heat loss is accurately measured by enhancing the migration of perspiration into an appropriate part of the sensor.

SUMMARY OF THE INVENTION

To achieve the above and other objects, the present invention discloses a novel method and apparatus for determining caloric expenditure by measuring all components of heat flow. It is small, portable, relatively inexpensive, and can be worn on the subject's body with no significant limitation on motion or mobility. The present invention utilizes a modified heat flow sensor element that is superior to heat flow sensors currently used, which fail to measure evaporative heat loss. Currently, only devices such as whole body calorimeters are capable of measuring all components of heat loss. As previously stated, these devices are large, expensive, relatively immobile, and limit the activity of the subject.

In order to improve the measurement of evaporative heat loss, the novel heat flow sensor element of the present invention can take on a specific construction such that the migration of evaporative fluid towards a center of the sensor element is enhanced. That is achieved in the present invention by inducing electroendosmosis by appropriately placing and biasing electrodes in the sensor element to enhance the migration of the evaporative fluid toward an active region of the sensor.

As a further way to improve the measurement of evaporative heat loss, the novel heat flow sensor of the present invention can take on a specific construction such that the active sensing elements are thermocouples which are placed at an edge of a sensor, so that a distance that perspiration has to migrate to an appropriate sensing position is reduced.

As additional features to enhance measuring evaporative heat loss with a heat flow sensor element, the present invention can optionally include a design of a sensor element with an overlay material which allows the evaporating fluid to migrate from the monitored surface (i.e., skin) to the ambient air side of the heat flow sensor element and subsequently to evaporate from the surface of the heat flow sensor element. To further facilitate the measurement of evaporative heat loss, the present invention can optionally create a substantially uniform temperature over the ambient air surface of the heat flow sensor and the surrounding measured surface. This can be accomplished using a thermally conductive layer which is placed over the ambient air surface of the heat flow sensor element and overlapped onto the measured surface.

BRIEF DESCRIPTION OF THE DRAWINGS

A more complete appreciation of the present invention and many of the attendant advantages thereof will be readily obtained as the same becomes better understood by reference to the following detailed description when considered in connection with the accompanying drawings, wherein:

FIGS. 8(a) and 8(b) show a further preferred sensor for measuring heat loss of the present invention;

DETAILED DESCRIPTION OF THE PREFERRED EMBODIMENTS

Although the present invention has many applications, the following discussion will focus on the sensing of caloric expenditure, for example, by measuring heat flow from a living being (human or animal) where the surface that is monitored is skin and the fluid through which the evaporative component of heat flow occurs is perspiration the term perspiration as used herein includes sensible or insensible fluid loss and is not limited to fluids which include salt, etc. This, however, is not the only application of the present invention. Other uses of the present invention include, for example, optimization of evaporative coolers.

The present invention measures conductive, convective, radiant, and evaporative heat flow using a modified heat flow sensor element.

Figure 1:
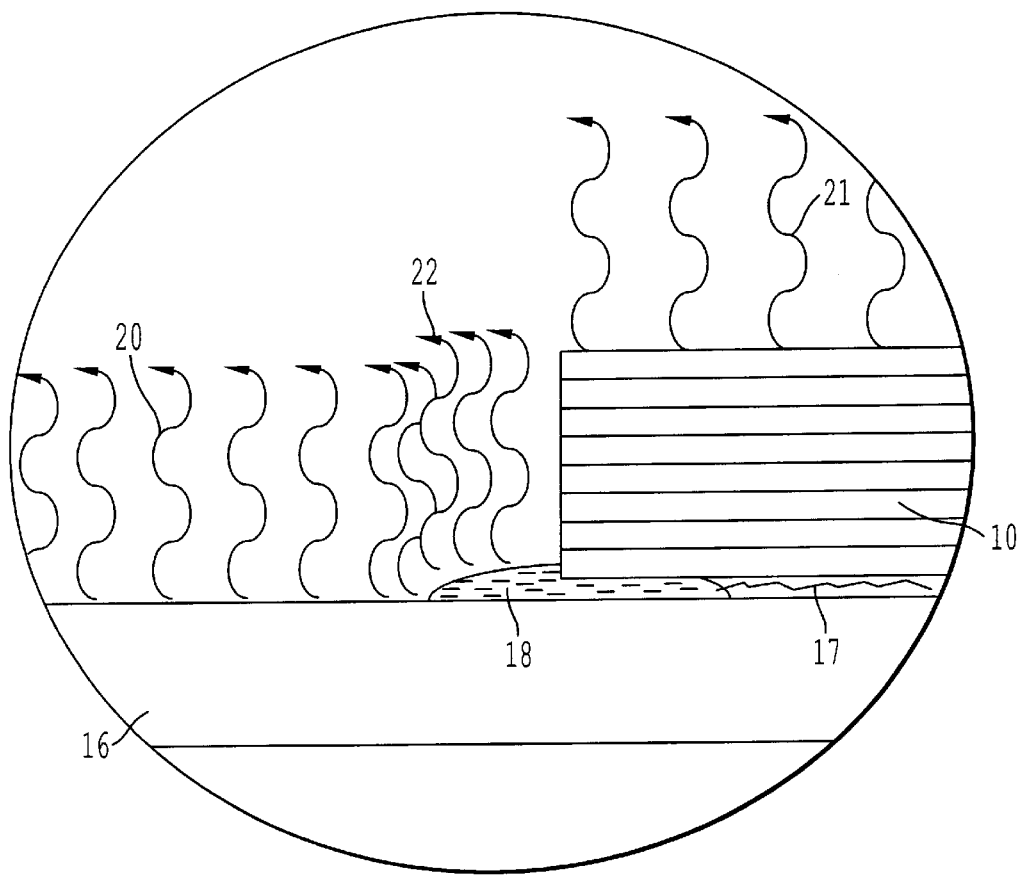
FIG. 1 is a cross-sectional view of a background heat flow sensor as presently used.

Evaporative heat loss occurs when perspiration on the skin surface evaporates. FIG. 1 is a cross-sectional view of a background heat flow sensor element as typically used. In this arrangement the heat flow sensor element 10 traps perspiration 17 against the subject's skin 16. This prevents the perspiration 17 from evaporating and prevents evaporative heat loss from the area of skin 16 covered with the heat flow sensor element 10. Since the heat flow sensor element 10 is not measuring evaporative heat flow, which is occurring on the surrounding skin 16, the heat flow measurement is not representative of the heat loss 20 on the surrounding skin 16. This error will cause the estimated heat loss 21 to be lower than the actual heat loss 20 by an amount equal to the heat loss due to evaporation. As a result of the heat flow sensor element 10 preventing the evaporation of perspiration under the sensor 17, perspiration 17 will accumulate under the sensor 10 and some perspiration 18 will leak out, and collect in the region surrounding the sensor 10. This collection of perspiration 18 around the edge of the heat flow sensor element 10 will cause an increased heat loss 22 in the region surrounding the sensor 10. Traditional sensor element 10 design places the sensing elements in the center of the sensor element 10, away from the edges, so that such traditional sensor elements 10 are most sensitive in the center where the sensing elements are. Since such background heat flow sensor elements 10 are most sensitive in the center of the sensor area and least sensitive at the fringe area, the increased heat loss 22 in the area surrounding the sensor 10 will not be detected. Further, increased losses at the edges of the sensor 10 would cause local cooling, thus decreasing convective and radiant heat flow measured by the sensor 10.

Figure 2:
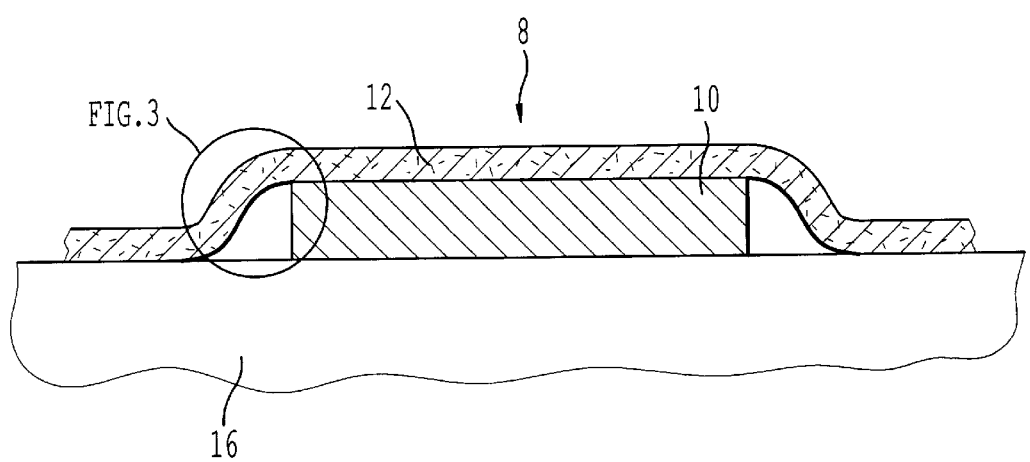
FIG. 2 is a cross-sectional view of a preferred embodiment of the present invention in use.
Figure 3:
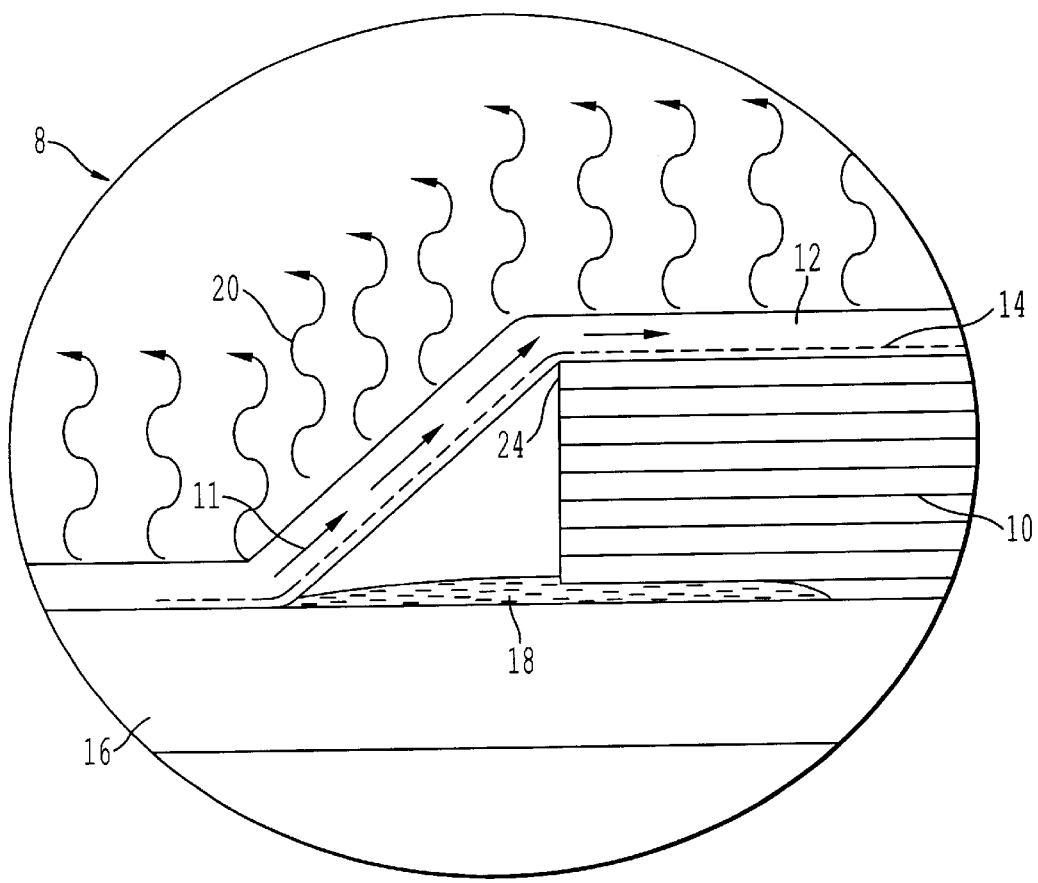
FIG. 3 is a closeup of the portion of FIG. 2 shown encircled.

The inventors of the present invention have already developed an improved heat flow sensor which minimizes and compensates for the shortcomings of such background heat flow sensors element 10 so that evaporative heat flow can be measured. One embodiment of such an improved heat flow sensor, generally, 8, is depicted in FIGS. 2 and 3. In that heat flow sensor 8 heat flow sensor element 10 is positioned on a surface 16, such as skin, as will subsequently be described.

In order to enhance inducing evaporative heat loss on the ambient air side 24 of the heat flow sensor element 10, the heat flow sensor 8 provides an overlay material 12 which allows the perspiration build-up 18 around the fringe of the heat flow sensor element 10 to migrate through the overlay material 12 as illustrated by the arrows 11, to the ambient air side 24 of the heat flow sensor 10. This migration enhances allowing perspiration to evaporate from the outer surface 24 of the heat flow element 10, which simulates the evaporative heat loss which is occurring on the subject's skin surface 16. Preferably, the overlay material 12 has a perspiration evaporation rate similar to that of the skin of the subject 16 under the same conditions. This evaporation rate typically can vary as much as and is preferably within the range of 20 g/m2 /day to 100 g/m2 /hr.

The overlay material 12 allows moisture to migrate onto the surface of the sensor element 10, but other techniques could also be used to cause the migration of moisture, such as by utilizing hydrophilic surface treatments or coatings, etching grooves into the sensor surface, etc.

The overlay material 12 should be capable of "imbibing" evaporative fluid, such as perspiration, preferably "wicking" the perspiration from the skin surface 16 to the ambient air side 24 of the heat flow sensor element 10. Overlay materials which appear to function best are constructed of leather, synthetic membranes, tight weave fabric, etc., although other materials could be utilized. An example of a synthetic membrane suitable as an overlay material is manufactured by Millipore. Other examples of suitable synthetic membranes include those sold under the trade names Thermipor, and Versapor.TM. manufactured by Gelman Sciences, Inc., Ann Arbor, Mich.

In general, the thinner the overlay material 12 is, the better the process works. Additionally, it has been found that overlay materials having 1–20 micron openings are particularly well-suited to "wicking" the perspiration build-up 18 from the measured surface 16 to the ambient air side 24 of the heat flow sensor element 10. An example of suitable tight weave material is Spectra/Mesh, manufactured by Spectrum of Los Angeles, Calif.

To further reduce measurement error, the heat flow sensor 8 can include a thermally conductive layer 14 placed across both the ambient air side 24 of the sensor element 10 and a portion of the surrounding skin surface 16. This creates a substantially uniform heat flow across both the skin surface 16 and the top 24 of the heat flow sensor element 10 so that the top surface 24 of the heat flow sensor element 10 will sense substantially the same heat flow as is occurring across the surrounding skin surface 16. This helps to correct heat flow variation caused by less perspiration across the center surface compared to the edges, and thus less evaporation, on the top 24 of the heat flow sensor element 10 than on the skin surface 16. Preferably, the thermally conductive material is selected from the group consisting of metal foil, including, by way of example but not limitation, copper, aluminum, stainless steel, and gold foils, vacuum deposited metal film, and thermally conductive plastics, and preferably has a thickness ranging from about 3000 .ANG. to 2 mils.

Although preferably the heat flow sensor 8 contains both an overlay material and a thermally conductive layer, the heat flow sensor 8 could also include the use of either element alone.

In order to prevent artificial heat retention in the tissue surrounding the heat flow sensor 8, the method of fastening the apparatus to the user should not inhibit heat flow. If the method of fastening the apparatus to the user traps heat against the skin surface, i.e. it insulates, there is a danger that the artificially increased skin temperature will cause a measurement error by the heat flow sensor. Preferably, therefore, the straps used for mounting heat flow sensor 8 use an open weave material, preferably having openings of ⅛–¼ inch and over 95% open area, to fasten the device to the user; however, other materials may also be used.

In a preferred method, multiple heat flow sensors 8 each having overlays 12 and/or thermally conductive layers 14 are positioned at various locations on the subject's body, to determine a total heat loss value for the subject. In another preferred embodiment, a single heat flow sensing apparatus 8 is placed at a location on the subject's body that is typical of heat loss for that subject. The subject's trunk or extremities near the trunk are usually representative of heat loss. However, such typical regions may also vary from subject to subject, and may be determined by applying multiple sensing apparatus 8 to the subject, evaluating each sensor individually and identifying the sensor or sensors that most nearly represent the total heat loss for all sensors for that subject. Once a "typical" region for heat loss is identified for that subject, the subject need only use one sensor 8 attached to that typical region.

In a preferred embodiment, the sensing apparatus 8 is attached to the wearer with, for example, an elastic armband which may be fabricated of an open weave material that allows the wearer to exercise freely. The heat flow information may be continuously monitored and recorded by a microcontroller or analog device capable of converting heat flow information into caloric expenditure information, both in terms of rate of caloric expenditure and cumulative caloric expenditure. Such microcontrollers include, by way of example, those available from Intel, including the Intel Pentium family.

Calorie expenditure may be calculated in a number of ways from the measure of heat flow obtained from the methods and apparatus of the present invention. A preferred method is based on the following equation:

Calorie expenditure (k–cal)=total body surface area($m2$)×fraction of body surface sampled by each sensor (1 for one sensor sensing typical region of heat flow)×heat flux(k–cal/$m2$ /min.)× time of sensing (min.).

The microcontroller is preferably programmed to continually monitor, record, and total heat flux for the subject, thereby allowing both an instantaneous rate of calorie expenditure and a total caloric expenditure for the subject to be monitored.

Figure 4:
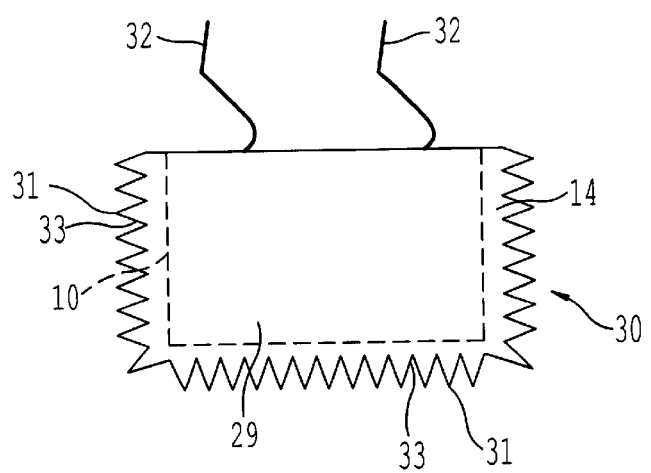
FIG. 4 is a schematic plan view of a background sensor for measuring heat loss as developed by the inventors of the present invention.

As illustrated in FIG. 4, the thermally conductive layer 14 may include center surface area 29 and a fringe region, generally 30, extending beyond the perimeter of the sensor element 10. This fringe region 30 may comprise a series of "fingers" 31 formed in the thermally conductive layer 14. The fringe area 30 preferably is located about a substantial portion of the periphery of the heat flow sensor element 10, but may exclude that portion through which the wire connectors 32 of the heat flow sensor element 10 pass. As illustrated, the fingers 31 have an open area 33 between adjacent fingers.

The inventors of the present invention, however, have recognized that the sensor of FIG. 4 can be improved upon.

That is, a significant requirement for accurate measurement of heat flow from a human or animal body is to capture as accurately as possible evaporative losses. That is achieved by mimicking the losses from the surface of the skin from the surface of the sensor 8. In order to effectively achieve such a mimicking operation, the perspiration must migrate onto the surface to the sensor, and more specifically onto an active area of the sensor element 10, which is the center of the sensor element 10.

Figure 5:
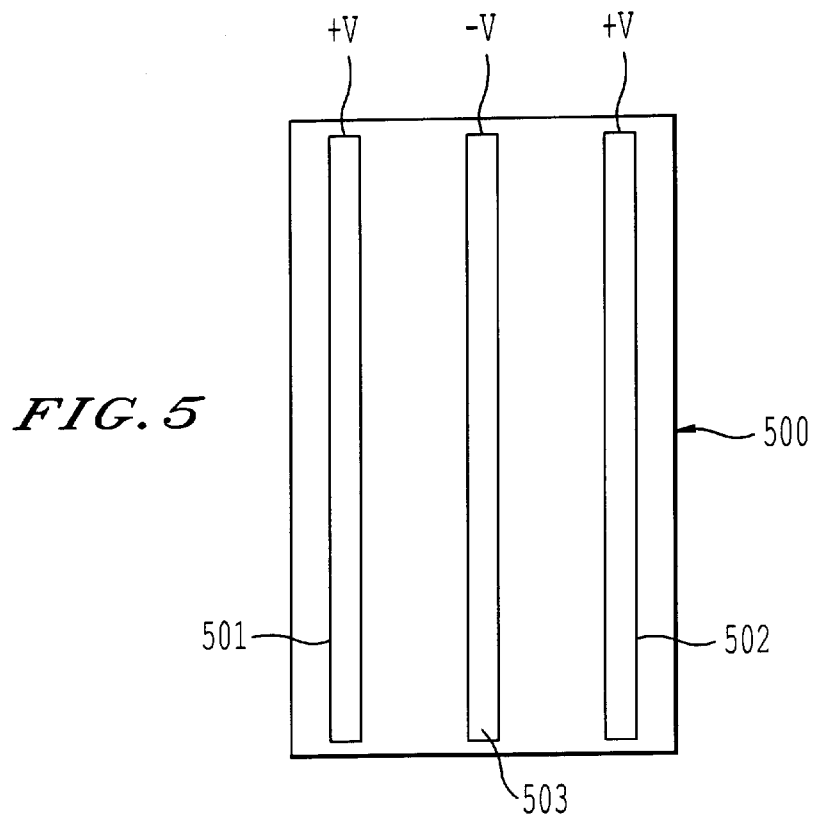
FIG. 5 is a schematic plan view of a first preferred sensor for measuring heat loss of the present invention.
Figure 6:
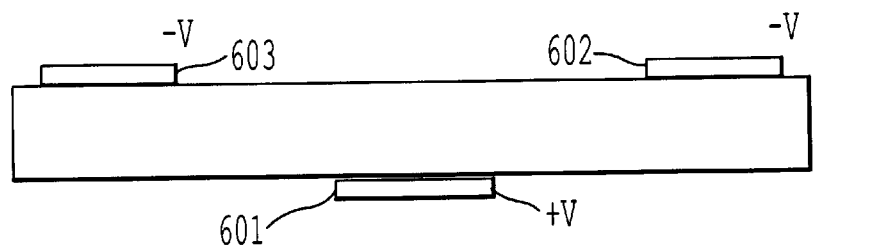
FIG. 6 is a cross-sectional view of a second preferred sensor for measuring heat loss of the present invention.

To further improve the sensing of perspiration by promoting the migration of perspiration from edges of a sensor element into the central active area of the sensor element two novel sensor designs as shown in FIGS. 5 and 6 of the present invention have now been developed by the present inventors.

FIG. 5 shows a first example of a novel sensor design of the present invention. In FIG. 5 element 500 indicates the sensor of that embodiment of the present invention, which essentially corresponds to the sensor 10 shown in FIGS. 1–4, i.e., the sensor 500 of FIG. 5 is utilized for the sensor 10 in FIGS. 1–4.

In FIG. 5 the same sensor construction as sensor 10 in FIGS. 1–4 is utilized except that the sensor 500 of FIG. 5 includes electrode elements 501, 502, and 503 on the surface. Electrodes 501 and 502 have a positive electric field applied thereto and electrode 503 has a negative electric field applied thereto. The electrode 503 is located in the center of the sensor 500 between electrodes 501 and 502, and thus is at the active region of the sensor 500.

The sensor 500 of FIG. 5 operates under a principle of electroendosmosis in which water, i.e., the perspiration from an evaporative loss, moves in response to an applied electric field from a positive electric field to a negative electric field. In the embodiment of FIG. 5 the perspiration which reaches the end of the sensor 500 is migrated by electroendosmosis from the end of the sensor 500 towards the center of the sensor 500 by the electric charge induced by the electrodes 501, 502, 503. The perspiration is migrated away from the positive electrodes 501, 502, i.e., those electrodes which receive a positive voltage, at the edges of the sensor 500 and towards the negatively biased electrode 503 in the center of the sensor 500. As the electrode 503 is the central electrode which is at an active region of the sensor, with such a structure of the present invention the perspiration to be sensed is migrated to an appropriate position on the sensor 500.

In the sensor 500 of FIG. 5 a cross-sectional view is not shown but it is noted that the electrodes 501, 502, and 503 would typically be provided at a top surface of the sensor 500 to receive the perspiration migrated as shown by arrows 11 in FIG. 3, i.e., the perspiration migrates as shown by arrows 11 in FIG. 3 to the top surface of the sensor 500 and thereby the electrodes 501, 502, 503 are preferably provided at the top surface of the sensor 500.

FIG. 6 shows a second embodiment of an improved sensor design of the present invention operating on the process of electroendosmosis but in a depthwise direction. That is, FIG. 6 shows in cross-sectional form a further sensor structure 600 of a further embodiment of the present invention. The sensor structure 600 of FIG. 6 is substantially the same as the sensor 10 of FIGS. 1–4 except that electrode elements 601, 602, and 603 are provided.

In the sensor 600 of FIG. 6 a positively biased electrode 601 is provided at the bottom surface of the sensor 600, i.e., at a surface which is to contact the skin of the body. Further, other electrodes 602, 603 having a negative electric field applied thereto are provided at a top surface of the sensor 600 above the electrode 601. Again operating on the process of electroendosmosis, perspiration against the skin of the body migrates through a depth-wise direction of the sensor 600 from the positive biased electrode 601 to the negative biased electrodes 602, 603, and thereby is provided at an appropriate point, at the sensor 600 to accurately reflect evaporative losses. In the embodiment shown in FIG. 6, the positively biased electrode 602 is positioned in a center of the sensor 600 whereas the negatively biased electrodes 602, 603 are provided at edges of the sensor 600. With such a positioning the evaporation can more accurately wick evaporation from the skin surface.

It is also possible, however, to put the negatively biased electrodes 602, 603 directly above the positively biased electrode 601.

Utilizing the sensor structures as shown in FIGS. 5 and 6 can improve the operation of a sensor in determining evaporative losses.

Figure 7:
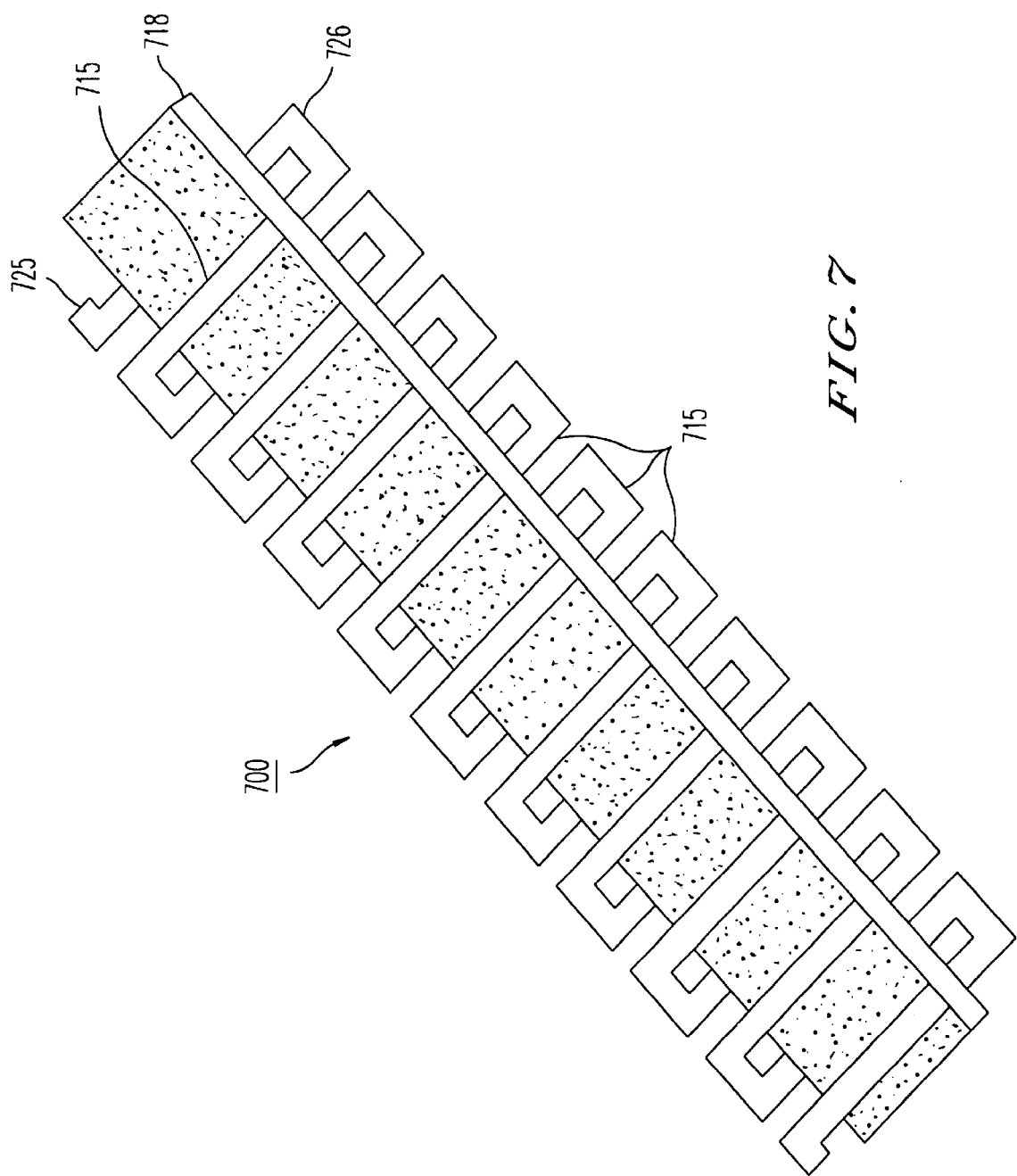
FIG. 7 shows a background heat flow sensor utilizing thermocouples.

The novel sensors 500 and 600 of respective FIGS. 5 and 6 operate on the basis of electroendosmosis in which an electrical bias is used to assist in the migration of perspiration to appropriate points on a sensor. An alternative approach, however, recognized by the present inventors to allow perspiration to more easily migrate onto an active area of a sensor is to reduce at least one dimension of the sensor, to thereby decrease the distance the perspiration has to migrate. In that context, the sensor element 10 can take the form of a thermocouple utilized to measure heat loss across an interlayer. A structure of a background thermocouple sensor is shown in FIG. 7. As shown in FIG. 7, a background thermocouple sensor 700 includes an interlayer 710 across which a difference in temperature is measured. That is, the thermocouple sensor 700 has a structure to measure a temperature difference between a bottom of the interlayer 710 and a top of the interlayer 710. The thermocouple sensor 700 of FIG. 7 achieves that operation by forming plural thermocouples 715 at a center point of the interlayer 710 both on the top and the bottom of the interlayer 710, although only the top thermocouples 715 are shown in FIG. 7. Those thermocouples 715 are formed at the junction of first and second thermocouple elements 720 and 725.

However, with such a background thermocouple sensor the perspiration has to migrate to the point at which the thermocouples 715 are located to provide an accurate heat flow measurement, meaning that the perspiration has to migrate to the center of the interlayer 710. As a result, such a background thermocouple sensor 700 has the drawback that the perspiration still has a significant path to migrate.

A further approach of the present invention is to utilize a thermocouple sensor which can reduce the path distance that perspiration must migrate to reach the active thermocouple elements, and which can thereby provide a more accurate measurement of heat flow and evaporation. Such a novel thermocouple sensor element of the present invention is shown in FIGS. 8(a) and 8(b).

FIGS. 8(a) and 8(b) show a further construction of a sensor 800 according to the present invention which can be utilized as the sensor element 10.

The sensor 800 structure of FIGS. 8(a) and 8(b), in which 8(b) shows a depthwise cross-sectional view and FIG. 8(a) shows a top view, includes asymmetrical thermocouples 815, 817 such that longer thermocouples 815 are formed on the right hand side of FIG. 8(b) and shorter length thermocouples 817 are formed on the left hand side. The structure of the heat flow sensor 800 of FIGS. 8(a) and 8(b) enhances the migration of perspiration to the active area of the sensor by reducing the distance the perspiration must migrate to reach the active sensing areas of the thermocouples. That is, with the novel sensor structure 800 of FIGS. 8(a) and 8(b), the active thermocouple elements 815, 817 are formed near the edge of the sensor, so that the perspiration only has to migrate a small distance to reach the active thermocouple portions 815, 817. Such an operation enhances the heat flow sensing for similar reasons as discussed above. The sensor 800 also includes, as shown in FIG. 8(b), cover layers 820 for protection of the thermocouples 815, 817 and for assisting migration of moisture to the thermocouples, particularly when the outer covers 820 are formed of the overlay material 12 as discussed above.

As also discussed above, in one feature of the present invention an overlay material 12 can be provided on a sensor element. In a preferred embodiment of the present invention that overlay material 12 can be formed of a membrane with a novel woven design of two different fibers.

That is, a further feature of the present invention is to utilize a membrane as overlay material 12 with a specific construction. One feature of the present invention is to utilize a specific structure of a membrane so that wicking properties of the membrane in one direction can be enhanced without adversely increasing its evaporative surface area. Certain threads, such as under the trade name CoolMax by Dupont, which are Dacron fibers with a convoluted diameter, are engineered to effectively wick perspiration in order to effect greater cooling. Such a material, however, also would present a significantly higher evaporative surface area than a simple solid thread. Thus, if a membrane was formed exclusively from such threads as CoolMax, that would result in an increase in evaporation compared to skin, and would thereby result in an overestimation of calorie expenditures.

Figure 9:
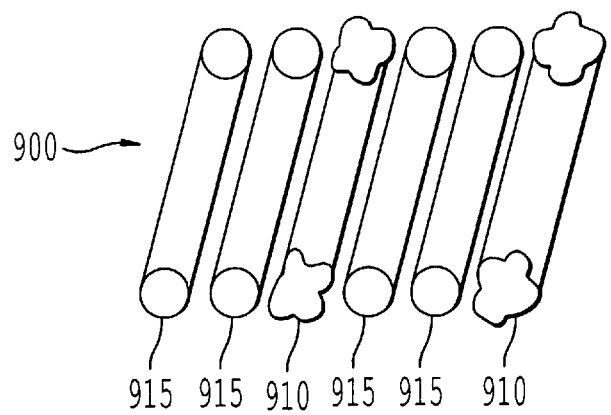
FIG. 9 shows a structure of a novel membrane used in a heat flow sensor of the present invention.

One feature in the present invention, as shown in FIG. 9, is to form a membrane 900 by weaving in a relatively small number of threads 910 such as CoolMax with a majority of solid threads 915 of monofilaments of Nylon fiber, for example in a ratio of 1 CoolMax Fiber to 2 Nylon fibers. With such a structure, wicking across the sensor would be enhanced without resulting in a significant increase in surface area. Further, the threads should be weaved in one direction, for example the weft. In the assembly of a sensor, the membrane would be positioned to cause the threads to cross over the heat flow sensor as the overlay 12.

Figure 10:
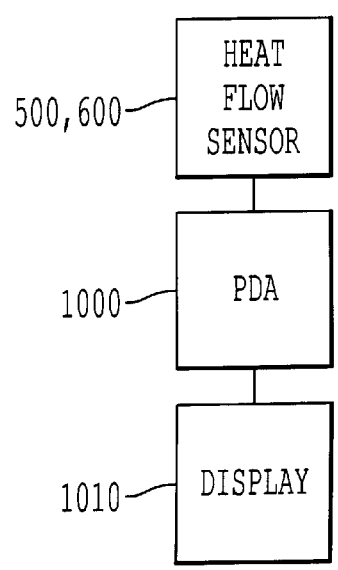
FIG. 10 shows the attachment of the sensor of the present invention in a preferred embodiment of the present invention.

FIG. 10 shows a construction of the sensor of the present invention to improve the ability to relay the information detected by the sensor.

That is, and as noted above, the inventors of the present invention have recognized that it may often be desirable for a user of a heat flow sensor to take the information detected by the heat flow sensor and place it into a device such as a personal computer, a PDA (personal digital assistant), etc. In that way the user could manipulate the data, store the data in a table for comparison purposes, display the data in different graphical forms, etc.

In FIG. 10 such a structure is shown in which the heat flow sensors 10, 500, 600, 700 are connected to a PDA. One of the most common PDAs is the Palm Pilot, but of course many PDAs could be utilized including those operating on the Palm Operating System, Microsoft CE, Pocket PC Operating System, and others. The heat flow sensors 10, 500, 600, 700 can provide the data to the PDA 1000, or alternatively a PC, etc. by any well known means such as by a line connection, wireless communication, etc.

Further, the PDA 1000 is connected to a display 1010. That display 1010 can be an integral part of the PDA or can be a separate display, such as the separate display of a personal computer.

Thus, in the present invention the heat flow sensor communicates with a data logger/output device, and/or a PC, and/or a PDA, and/or any other type of output device capable of receiving the signal through either radio frequency (RF), infra-red transmission (IR), hard-wired communication, or other means. The device may also be completely integrated as one unit including both a device to generate and capture a signal, and to then translate and display results, or it may include separate units to perform those functions.

Thus, the measuring device includes a communication device enabling wired or wireless connection between the heat-flow sensor, and/or thermocouple, or thermistor or other heat-flow measuring device for the measurement of calorie expenditures to a data logger, a PC, a PDA, or other output device. The PC or PDA or data-logger translates the signal from the heat-flow sensor into calorie expenditures via software utilizing stored information. Feedback of this information to the user will help the user to know their caloric expenditure. This information can be useful for fitness monitoring, well-being monitoring, weight management, etc.

The PC or PDA or data-logger may also contain stored information about previous calorie expenditures over the previous minute, hour, day, week, month or year or other time interval. This information can be used for various uses including comparisons to previous measurements as well as comparisons to calorie intake. Additionally, the caloric and nutritional content of food can be stored in this database for use in comparing the calorie intake of food with the caloric expenditure of the user. This information is then used to determine level of fitness, well-being, weight management, etc.

Obviously, numerous additional modifications and variations of the present invention are possible in light of the above teachings. It is therefore to be understood that within the scope of the appended claims, the present invention may be practiced otherwise than as specifically described herein.

What is claimed is:

1. An apparatus for determining caloric expenditure by measuring total heat flow from the skin surface of a wearer of the apparatus comprising:
   a) a heat flow sensor configured to measure heat flow, said heat flow sensor including:
      a1) an interlayer; and
      a2) first and second thermocouple elements formed on a first surface near an edge of said interlayer.

2. An apparatus according to claim 1, further comprising:
   (b) an overlay material, at least a portion of which contacts said wearer's skin surface and another portion of which covers said heat flow sensor, said overlay material being capable of imbibing a fluid and allowing said fluid to migrate from said skin surface to the portion of said overlay material contacting said heat flow sensor such that said imbibed fluid can evaporate from said portion of said overlay material covering said heat flow sensor.

3. An apparatus according to claim 2, wherein said skin surface and said overlay material have essentially the same evaporation rate.

4. An apparatus according to claim 2, wherein said overlay material is selected from the group consisting of leather, synthetic membranes, and tight-weave fabrics.

5. An apparatus according to claim 2, further comprising:
   (b) a thermally conductive material located between said heat flow sensor and said overlay material to create a substantially uniform heat flow across said surface of said heat flow sensor.

6. An apparatus according to claim 5, wherein said thermally conductive material is selected from the group consisting of metal foil, vacuum deposited metal film, and thermally conductive plastics.

7. An apparatus according to claim 6, wherein both said overlay material and said skin have essentially the same evaporation rate.

8. An apparatus according to claim 1, further comprising:
   (b) an overlay material, at least a portion of which contacts said weaver's skin surface and another portion of which covers said heat flow sensor, said overlay material formed of a membrane including first Nylon™ fibers and second CoolMax™ fibers interwoven with said first Nylon™ fibers.

9. An apparatus according to claim 8, further comprising:
   (c) a thermally conductive material located between said heat flow sensor and said overlay material to create a substantially uniform heat flow across said surface of said heat flow sensor.

10. An apparatus according to claim 9, wherein said thermally conductive material is selected from the group consisting of metal foil, vacuum deposited metal film, and thermally conductive plastics.

11. An apparatus according to claim 1, further comprising:
   b) an output configured to provide data from said heat flow sensor to a computing device.

12. An apparatus for determining caloric expenditure by measuring total heat flow from the skin surface of a wearer of the apparatus comprising:
   a) heat flow sensor means for measuring heat flow, said heat flow sensor means including:
      a1) thermocouple means for forming thermocouple elements at an edge of said heat flow sensor means.

13. An apparatus according to claim 12, further comprising:
   (b) overlay means for imbibing a fluid and allowing said fluid to migrate from said skin surface to the portion of said overlay material contacting said heat flow sensor such that said imbibed fluid can evaporate from said portion of said overlay material covering said heat flow sensor.

14. An apparatus according to claim 12, further comprising:
   (b) thermally conductive means for creating a substantially uniform heat flow across said surface of said heat flow sensor means.

15. An apparatus according to claim 13, further comprising:
   (c) thermally conductive means for creating a substantially uniform heat flow across said surface of said heat flow sensor means.

16. An apparatus for determining caloric expenditure by measuring total heat flow from the skin surface of a wearer of the apparatus comprising:
   a) a heat flow sensor configured to measure heat flow, said heat flow sensor including:
      a1) at least one positively biased electrode; and
      a2) at least one negatively biased electrode.

17. An apparatus according to claim 16, wherein said at least one positively biased electrode includes two positively biased electrodes, and said at least one negatively biased electrode is positioned between the two positively biased electrodes.

18. An apparatus according to claim 16, wherein said at least one positively biased electrode is positioned near the skin surface of the wearer and said at least one negatively biased electrode is positioned above said at least one positively biased electrode in a depth direction of said heat flow sensor.

19. An apparatus according to claim 16, further comprising:
   (b) an overlay material, at least a portion of which contacts said wearer's skin surface and another portion of which covers said heat flow sensor, said overlay material being capable of imbibing a fluid and allowing said fluid to migrate from said skin surface to the portion of said overlay material contacting said heat flow sensor such that said imbibed fluid can evaporate from said portion of said overlay material covering said heat flow sensor.

20. An apparatus according to claim 19, wherein said skin surface and said overlay material have essentially the same evaporation rate.

21. An apparatus according to claim 19, wherein said overlay material is selected from the group consisting of leather, synthetic membranes, and tight-weave fabrics.

22. An apparatus according to claim 19, further comprising:
   (b) a thermally conductive material located between said heat flow sensor and said overlay material to create a substantially uniform heat flow across said surface of said heat flow sensor.

23. An apparatus according to claim 22, wherein said thermally conductive material is selected from the group consisting of metal foil, vacuum deposited metal film, and thermally conductive plastics.

24. An apparatus according to claim 23, wherein both said overlay material and said skin have essentially the same evaporation rate.

25. An apparatus according to claim 16, further comprising:
   (b) an overlay material, at least a portion of which contacts said weaver's skin surface and another portion of which covers said heat flow sensor, said overlay material formed of a membrane including first Nylon™ fibers and second CoolMax™ fibers interwoven with said first Nylon™ fibers.

26. An apparatus according to claim 25, further comprising:
   (c) a thermally conductive material located between said heat flow sensor and said overlay material to create a substantially uniform heat flow across said surface of said heat flow sensor.

27. An apparatus according to claim 26, wherein said thermally conductive material is selected from the group consisting of metal foil, vacuum deposited metal film, and thermally conductive plastics.

28. An apparatus according to claim 16, further comprising:
   b) an output configured to provide data from said heat flow sensor to a computing device.

29. An apparatus for determining caloric expenditure by measuring total heat flow from the skin surface of a wearer of the apparatus comprising:
   a) heat flow sensor means for measuring heat flow, said heat flow sensor means including:
      a1) means for migrating perspiration from an edge of said heat flow sensor means to a most active region of said heat flow sensor means.

30. An apparatus according to claim 29, further comprising:
   (b) overlay means for imbibing a fluid and allowing said fluid to migrate from said skin surface to the portion of said overlay material contacting said heat flow sensor such that said imbibed fluid can evaporate from said portion of said overlay material covering said heat flow sensor.

31. An apparatus according to claim 29, further comprising:
   (b) thermally conductive means for creating a substantially uniform heat flow across said surface of said heat flow sensor means.

32. An apparatus according to claim 30, further comprising:
   (c) thermally conductive means for creating a substantially uniform heat flow across said surface of said heat flow sensor means.

* * * * *